(12) United States Patent
Jeffery et al.

(10) Patent No.: US 12,714,416 B2
(45) Date of Patent: Aug. 25, 2026

(54) ANCHOR ASSEMBLY

(71) Applicant: FIELD ORTHOPAEDICS PTY LTD, Red Hill (AU)

(72) Inventors: Christopher Arnold Jeffery, Teneriffe (AU); Michael Maurer, Teneriffe (AU)

(73) Assignee: FIELD ORTHOPAEDICS PTY LTD, Red Hill (AU)

( * ) Notice: Subject to any disclaimer, the term of this patent is extended or adjusted under 35 U.S.C. 154(b) by 121 days.

(21) Appl. No.: 18/682,354

(22) PCT Filed: Aug. 4, 2022

(86) PCT No.: PCT/AU2022/050845
§ 371 (c)(1),
(2) Date: Feb. 8, 2024

(87) PCT Pub. No.: WO2023/015336
PCT Pub. Date: Feb. 16, 2023

(65) Prior Publication Data

US 2024/0350134 A1 Oct. 24, 2024

(30) Foreign Application Priority Data

Aug. 9, 2021 (AU) ................................ 2021902449

(51) Int. Cl.
*A61B 17/04* (2006.01)

(52) U.S. Cl.
CPC .. *A61B 17/0401* (2013.01); *A61B 2017/0414* (2013.01)

(58) Field of Classification Search
None
See application file for complete search history.

(56) References Cited

U.S. PATENT DOCUMENTS 6,511,498 B1 1/2003 Fumex
2013/0123810 A1* 5/2013 Brown .............. A61B 17/0401 606/144

(Continued)

FOREIGN PATENT DOCUMENTS

WO 2020252372 A1 12/2020

OTHER PUBLICATIONS

International Preliminary Report on Patentability for International Application No. PCT/AU2022/050845, dated Jul. 7, 2023, 6 pages.

(Continued)

*Primary Examiner* — Shaun L David
(74) *Attorney, Agent, or Firm* — CANTOR COLBURN LLP

(57) ABSTRACT

An anchor assembly includes an elongate and flexible anchoring implant for inserting into a bore of bone or tissue, the implant having proximal and distal ends with sidewalls extending therebetween, a suture having: first and second segments between the proximal and distal ends of the implant and passed through a first and second side wall portions of the implant, respectively. A bridging loop between the two segments, and at or adjacent an in-use upper portion of the implant that includes the proximal end; wherein each of the segments has respective terminal ends of the suture extending from the implant. Applying tension to the terminal ends, when implant is in bone or tissue, causes the proximal end to be drawn towards the distal end to effect change of the implant shape from elongate and radially narrow into axially shortened and radially extended configurations to deploy the implant in the bore.

16 Claims, 11 Drawing Sheets

(56) References Cited

U.S. PATENT DOCUMENTS

2013/0296934 A1* 11/2013 Sengun .............. A61B 17/0401 606/232
2014/0052178 A1* 2/2014 Dooney, Jr. ........ A61B 17/0401 606/232
2014/0052179 A1* 2/2014 Dreyfuss ............... A61F 2/0811 606/232
2014/0277133 A1 9/2014 Foerster
2015/0173739 A1* 6/2015 Rodriguez ....... A61B 17/06166 606/232

OTHER PUBLICATIONS

International Search Report for International Application No. PCT/AU2022/050845, dated Oct. 7, 2022, 6 pages.
Written Opinion for International Application No. PCT/AU2022/050845, dated Oct. 7, 2022, 6 pages.

* cited by examiner 120
100

120B
122B
112
122A
120A 120B
125B
124
125A
110
120A 125
200

125
200

200

142
144
125B
125A
124
110
120B
120A
140
100
1000'
122B
112
122A

ANCHOR ASSEMBLY

CROSS-REFERENCE TO RELATED APPLICATIONS

This application is a 35 U.S.C. § 371 National Stage patent application of PCT/AU2022/050845, filed on 4 Aug. 2022, which claims the benefit of Australian patent application 2021902449, filed on 9 Aug. 2021, the disclosures of which are incorporated herein by reference in their entirety.

TECHNICAL FIELD

The present disclosure relates to an anchor assembly for use in tissue repair.

BACKGROUND

Any references to methods, apparatus or documents of the prior art are not to be taken as constituting any evidence or admission that they formed, or form part of the common general knowledge.

Many orthopaedic surgical procedures involve the use of anchoring devices that attach soft tissue to bone. The positioning of anchor involves the drilling of holes or bores into which such anchor devices are placed. Soft anchors such as the commercially known Q-Fix anchors are well known and provide some key advantages over solid anchors made from metals or polymers such as Poly Lactic Acid (PLA) and these advantages include: 1) The use of a less-invasive implantation techniques (typically drilling smaller holes) since the soft anchors are less brittle 2) The ease of manufacture since soft anchors are much easier to manufacture compared to solid anchors; 3) Lower risk profile since there is no risk of a solid anchor becoming lodged in a joint or body cavity; 4) soft anchors generate a larger surface area and are therefore considered very strong.

Soft anchors also suffer from some disadvantages including: 1) Issues with deployment whereby the soft anchors fail to full engage with the walls of the bore or hole which results in the anchors becoming dislodged; 2) Less user friendly when compared with solid anchors and the insertion instruments are often highly mechanised and complex; 3) the currently known soft anchors can piston in the bone tunnel (resulting in a gap between the site of healing and the tissue) and as such have unreliable tensioning, and 4) soft anchors require deeper drill holes (as the full implant must be inserted and a working distance is needed to deploy)—which can result in the implant not being suitable for small extremity bones.

In view of the above, it is desirable to provide an improved anchor assembly which addresses at least some of the shortcomings of the prior art.

SUMMARY

In an aspect, the disclosure provides an anchor assembly for securing a tissue to a bone or tissue, the anchor comprising:

- an elongate and flexible anchoring implant for inserting into a bore of the bone or the tissue, the anchoring implant comprising a proximal end and a distal end with sidewalls extending therebetween,
- a suture comprising: a first suture segment extending between the proximal and distal ends of the implant, the first suture segment being woven through a first side wall portion of the implant; a second suture segment extending between the proximal and distal ends of the implant, the second suture segment being woven through a second side wall portion of the implant; a bridging loop extending between the first suture segment and the second suture segment, the bridging loop being located at or adjacent the proximal end of the anchoring implant; and wherein each of the first and second suture segments comprises respective terminal ends of the suture that extend from the proximal end of the anchor implant;
- wherein applying tension to the terminal ends of the suture, when the anchoring implant is located in the bone or the tissue, causes the flexible anchoring implant to change shape from an elongate and radially narrow configuration into an axially shortened and radially extended configuration so as to deploy the anchoring implant in the bore.

In an embodiment, each of the first and second suture segments comprises a respective distal loop to engage a thickness of the distal end portion of the anchoring implant.

In an embodiment, upon being tensioned the distal loop engages a thickness of the distal end portion of the anchor implant.

In an embodiment, upon being tensioned, the bridging loop engages a circumferential edge of the proximal end portion of the anchoring implant.

In an embodiment, the first and second suture segments are continuous with each other.

In an embodiment each of the first and second suture segments comprises:

- a first weave extending axially along the walls of the anchoring implant in a direction from the proximal end of the anchoring implant towards the distal end of the anchoring implant;
- a second weave extending axially along the walls of anchoring implant in a direction from the distal end of the anchoring implant towards the proximal end of the anchoring implant; and
- wherein the first and second weave for each suture segment are separated by the first locking loop of the suture that is located at the distal end of the anchoring implant.

An anchor assembly wherein the first and second weave for each suture segment are radially spaced apart from each other.

In an embodiment, the first and second weave for the first suture segment are radially spaced apart from the first and second weave for the second suture segment.

In an embodiment, the distal end of the anchor implant is closed. Preferably, the distal end of the anchor implant is closed by way of sealing or heat fusion of the distal end of the distal portion of the anchor implant.

In an embodiment, the terminal ends of the suture are attached to a respective surgical needle.

In an embodiment, the anchoring implant comprises a braided structure.

In an embodiment, the anchoring implant comprises a tubular structure in the elongate and radially narrow configuration.

In an embodiment, the suture comprises biodegradable materials.

In an embodiment, the terminal end of the second suture segment is turned and woven with a portion of the second segment into an internal portion of the implant.

BRIEF DESCRIPTION OF THE DRAWINGS

Preferred features, embodiments and variations of the disclosure may be discerned from the following Detailed Description which provides sufficient information for those skilled in the art to perform the disclosure. The Detailed Description is not to be regarded as limiting the scope of the preceding Summary of the Disclosure in any way. The Detailed Description will make reference to a number of drawings as follows.

DETAILED DESCRIPTION OF THE DRAWINGS

In the following description, a preferred embodiment of the present disclosure will be described. For purposes of explanation, specific configurations and details are set forth in order to provide a thorough understanding of the embodiments. However, it will also be apparent to one skilled in the art that the present disclosure may be practiced without one or more of the specific features described in the foregoing sections.

It is envisioned that the anchor assembly 1000 would have broad application in orthopaedic surgery. Applications outside of orthopaedic surgery may also be considered within the scope of use for the anchor assembly 1000 described herein.

Figure 1:
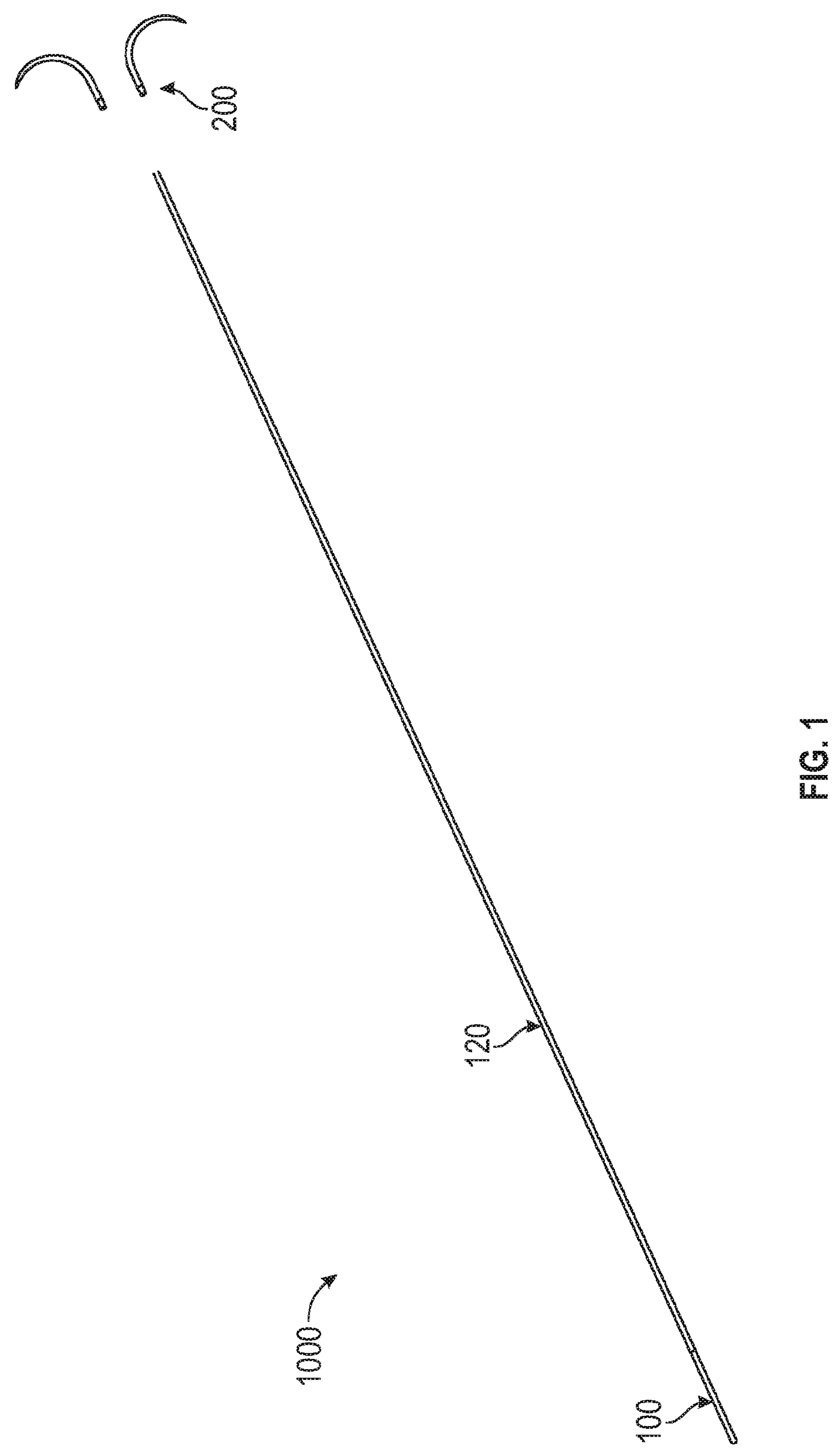
FIG. 1 is an exploded view of an anchor assembly 1000 in accordance with a preferred embodiment.
Figures 2A, 2B:
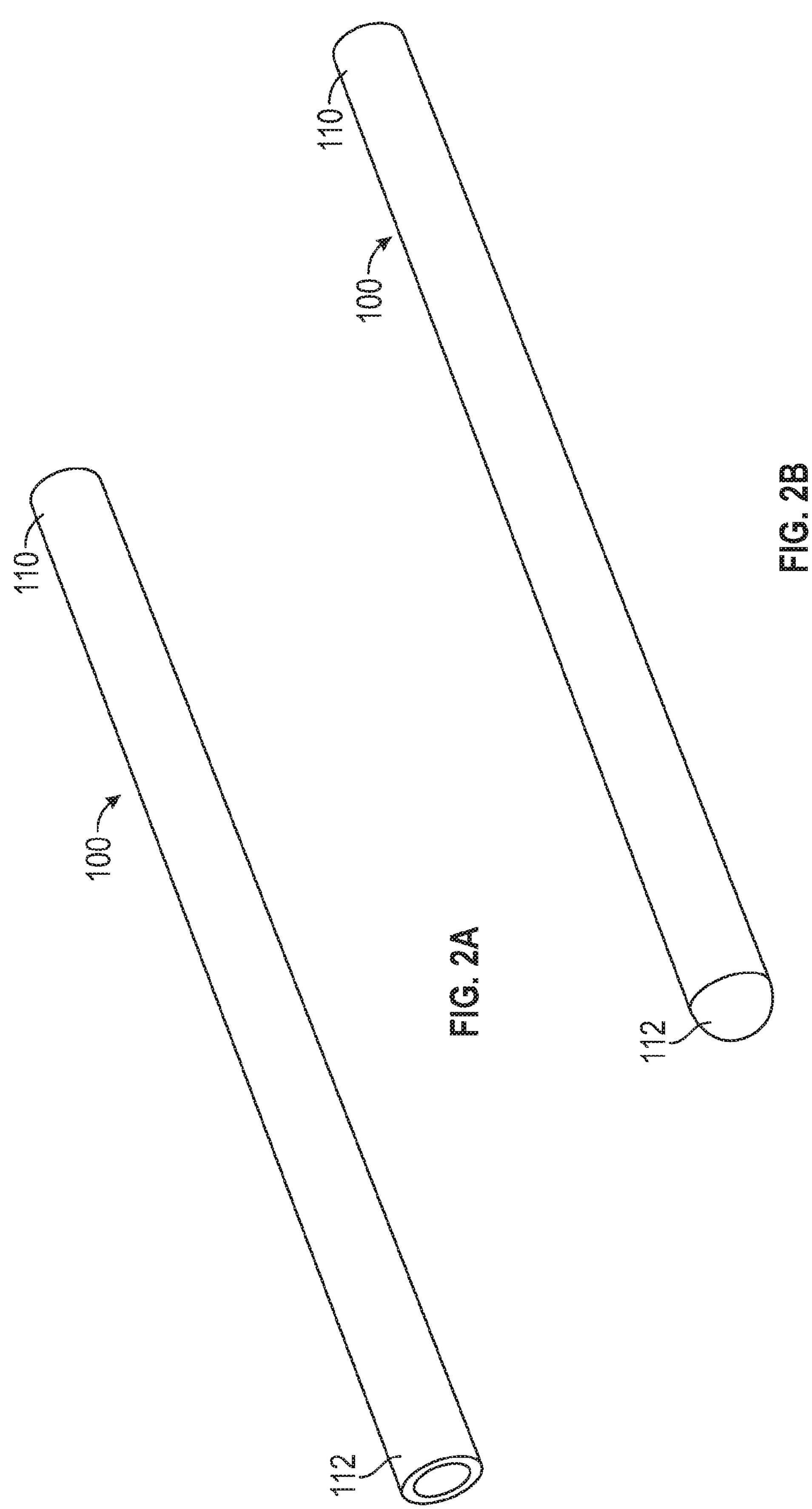
FIG. 2A is an isolated view of the soft anchoring implant 100 in which both ends 110 and 112 are open.
FIG. 2B is an isolated view of the soft anchoring implant 100 in which the distal end 112 has been closed.
Figure 3:
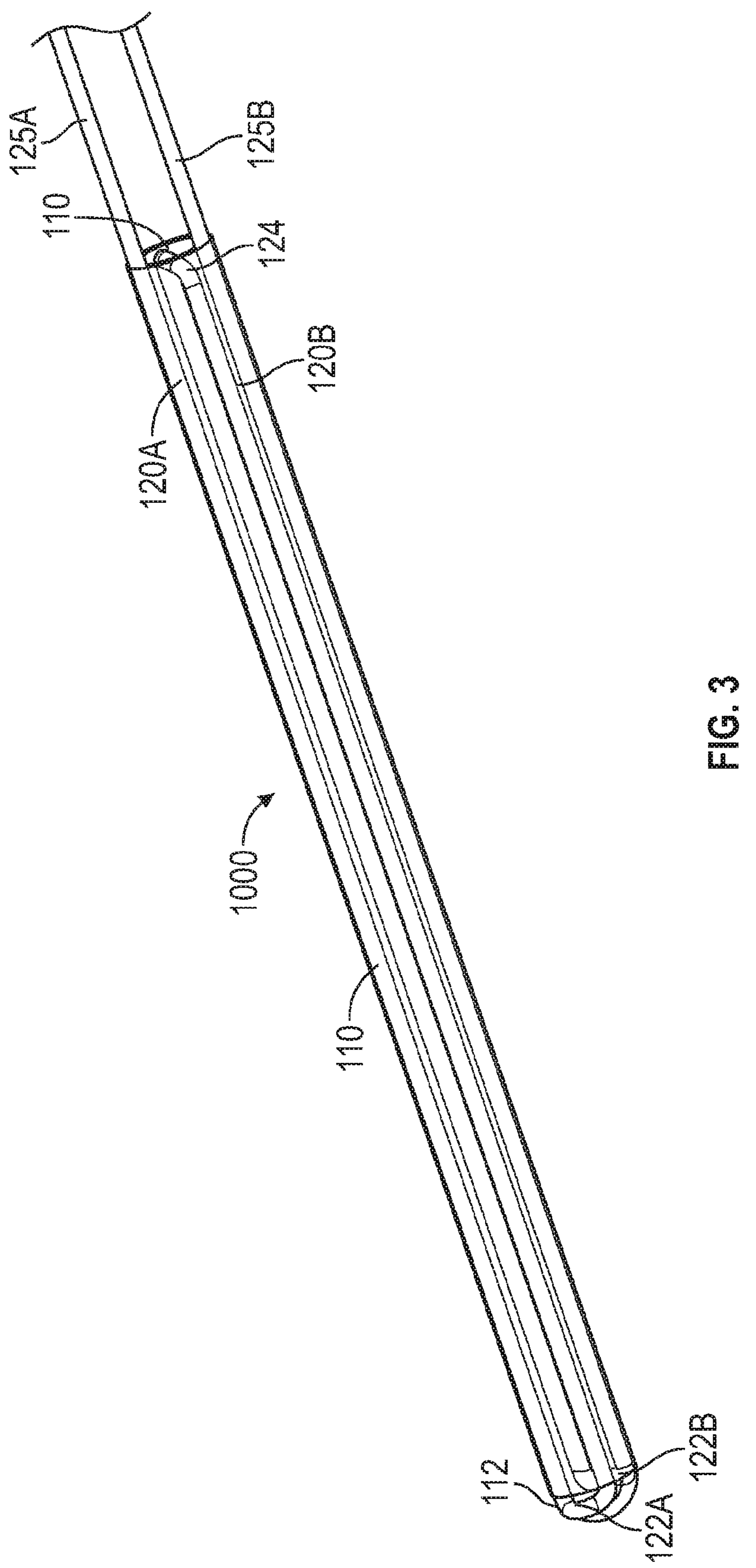
FIG. 3 is an enlarged view of the soft anchoring implant 100 in which the suture 120 has been shown woven into the body of the soft anchoring implant 100.

FIGS. 1 to 5 illustrate a preferred embodiment of an anchor assembly 1000 in which like reference numerals refer to like features throughout the specification. FIG. 1 is an exploded view of the anchor assembly 1000 comprising a soft anchoring implant 100 with a length of suture 120 woven through the anchoring implant 100 in a novel configuration with terminal ends of the suture 120 being attached to a respective surgical needle 200. The soft anchor implant 100 can be used as part of a tissue repair system and the soft anchor implant 100 is intended to anchor suture within bone or other hard tissue and allow for the further attachment of soft tissue as in an orthopaedic repair.

The soft anchoring implant 100, is three-dimensional, tubular shape with one open end (also referred to as the proximal end) 110 and one closed end (also referred to as the distal end) 112 and defining a resident volume (discussed in detail later). The size of the anchoring implant 100 is not limiting but it can be reasonably expected to be suitably in the range of 5 mm to 30 mm with an initial diameter being in the range of 2 mm to 5 mm. It is important to note that the dimensions of the anchoring implant 100 may be varied depending on the type of orthopaedic surgery being carried out. The soft anchor implant 100 is formed from a coarse braided material. The structure of the soft anchor implant 100 may be a braided structure such that pulling the entire braid along its axial length results in a narrow and long configuration (which is the initial position when the anchor implant 100 is inserted into a bore or hole drilled into tissue). In this configuration, it is understood that the length increases when the braided threads forming the anchoring implant 100 become substantially parallel. In the same way, when the ends of the braided anchoring implant 100 are drawn closer together by tensioning a suture 120 woven through the length of the anchoring implant 100, the braid contracts axially and expands radially, in this case by increasing the angle between the braided threads. This helically wound braid for the soft anchor implant 100 provides an advantage in that the structure can collapse and elongate naturally due to the alignment of the braids.

A length of suture 120 of the type that is typically used in orthopaedic repair procedures is woven through the braided body of the soft anchoring implant 100. We refer to FIGS. 4 and 5, in particular, to provide details on the manner in which the suture 120 is woven into the braided structure of the soft anchoring implant 100. The suture 120 comprises first and second suture segments 120A and 120B that are formed continuously with each other and extend between the proximal end 110 and the distal end 112 of the implant 100 in column weave pattern as illustrated below. Each of the first and second suture segments 120A and 120B comprises respective terminal ends 125A and 125B respectively that extend from the proximal end 110 of the anchor implant 100.

Figure 4:
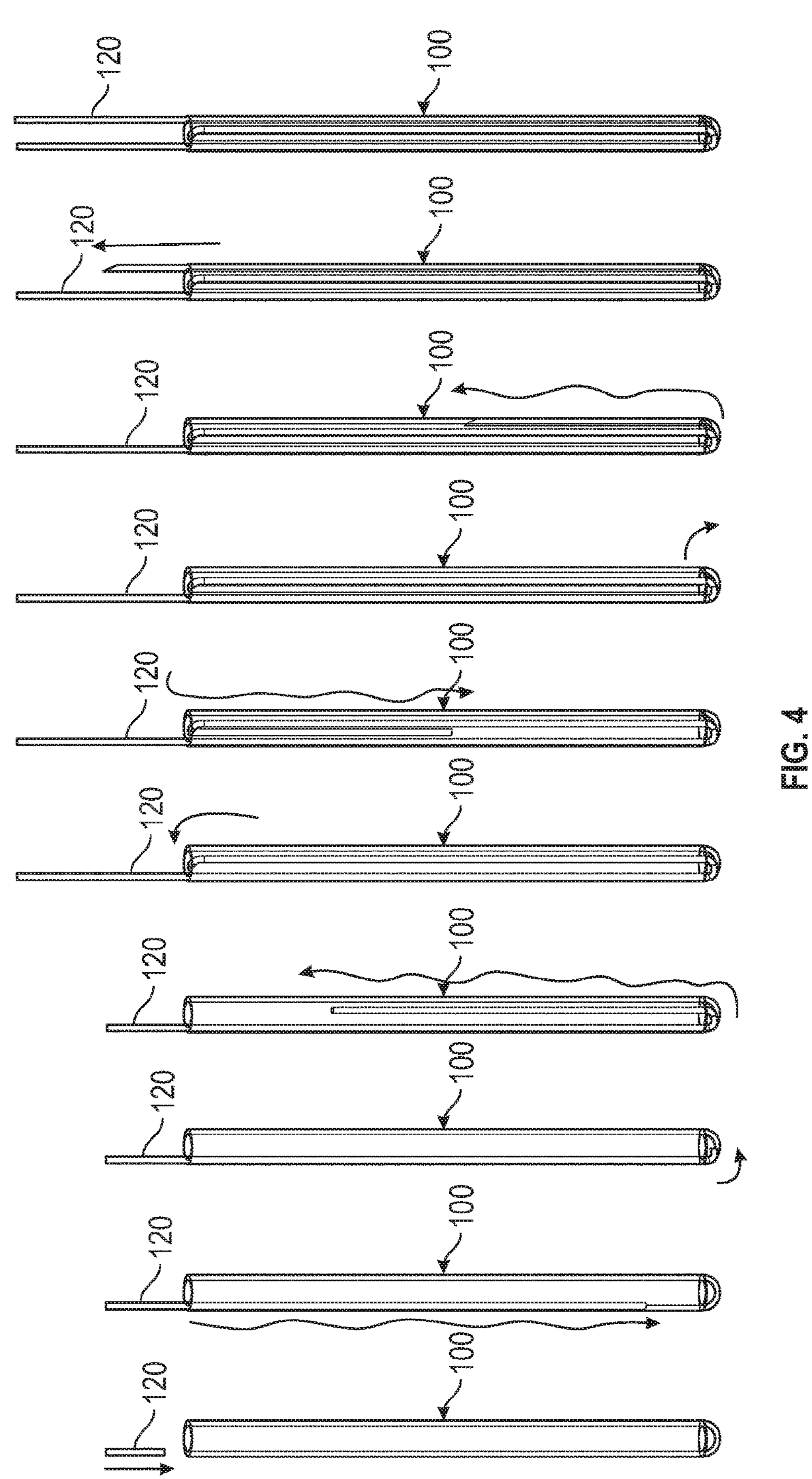
FIG. 4 depicts weaving steps 1 to 10 for weaving the suture 120 into the body of the soft anchoring implant 100 in a column weave (passing down from the proximal end 110 to the distal end 112 and then back up from the distal end 112 of the anchoring implant 100 to the proximal end 110 and then across the proximal portion of the anchoring implant 100 and then back down towards the distal end 112 before being woven back up towards the proximal end 110 of the anchoring implant 100.
Figures 5A, 5B:
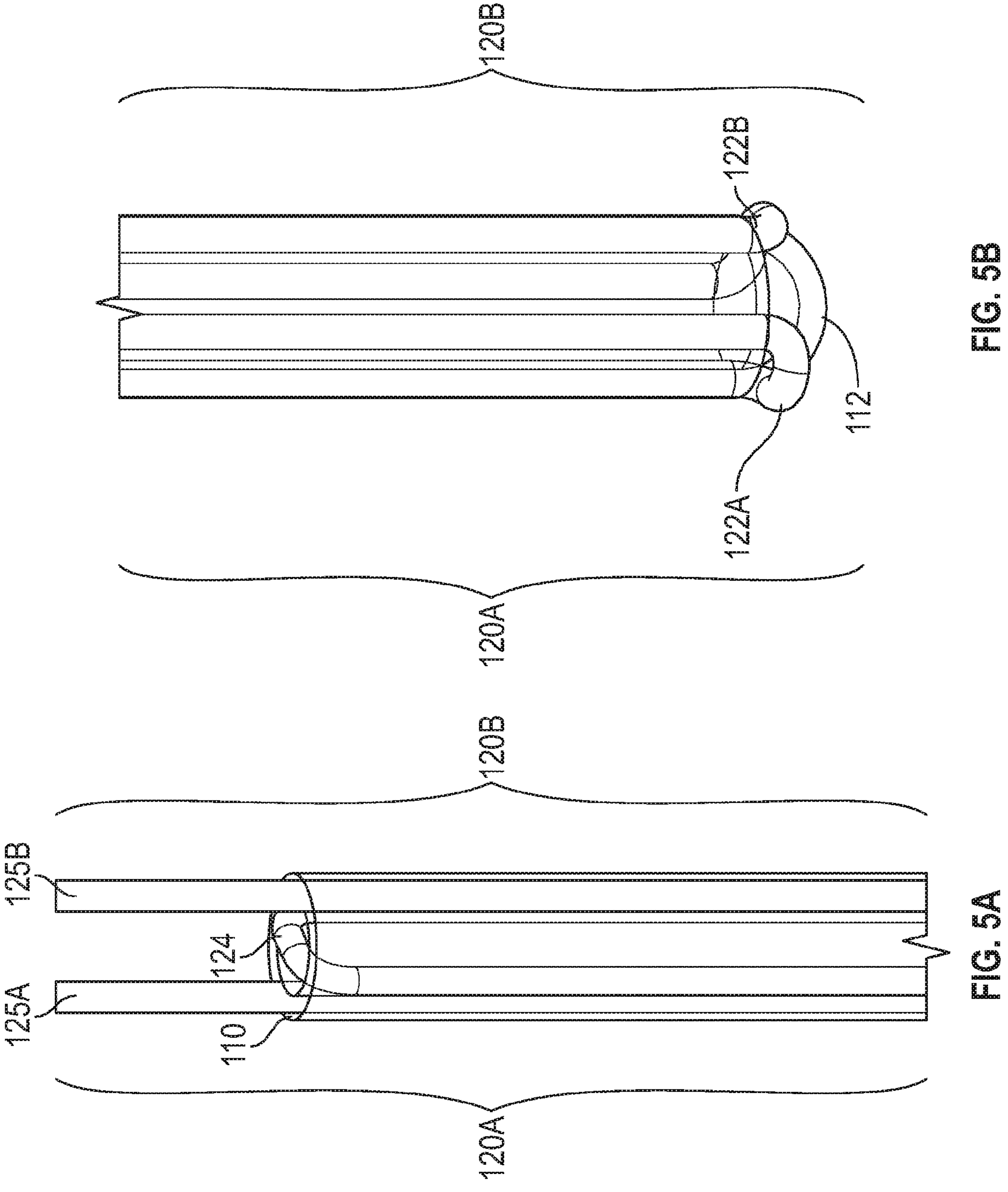
FIG. 5A illustrates the proximal end 110 of the soft anchoring implant 100.
FIG. 5B illustrates the distal end 112 of the soft anchoring implant 100.

Specifically, each suture segment 120A and 120B comprises a first weave extending axially along the walls of the anchoring implant 100 in a direction from the proximal end 110 of the anchoring implant 100 towards the distal end 112 of the anchoring implant 100 (see Steps 1 and 2 which depict the first weave for segment 120A and Steps 9 and 10 that depict the first weave pattern for segment 120B). Each of the segments 120A and 120B also comprises a second weave extending axially along the walls of anchoring implant 110 in a return direction from the distal end 112 of the anchoring implant 110 towards the proximal end 110 of the anchoring implant 110 (shown in Steps 4 and 5 for segment 120A and Steps 6 and 7 for segment 120B as shown in FIG. 4). The first and second weave for each suture segment 120A and 120B are separated by a respective distal loops 122A and 1228 of the suture that is located at the distal end 112 of the anchoring implant 110. The first and second weave for segments 120A and 120B are radially spaced apart across the circumference of the tubular cross section of the soft anchoring implant 100. Preferably the four weave patterns for the two suture segments 120A and 120B are radially spaced apart from each other by ninety degrees. Importantly, a bridging loop 124 is provided at or adjacent the proximal end 110 of the anchoring implant 100 to connect the suture segments 120A and 120B such that tensioning the loop 124 results in the loop 124 engaging a circumferential edge of a proximal end portion of the anchoring implant 100.

The novel woven configuration of the suture segments 120A and 120B is such that applying tension to the terminal ends 125A and 125B of the suture 120, causes the flexible anchoring implant 100 to change shape from the elongate and radially narrow configuration into an axially shortened and radially extended configuration so as to deploy the anchoring implant 100 in the bore. Importantly, the provision of the bridging loop 124 at the proximal end 110 of the anchoring implant 100 results in the proximal end 110 of the soft anchoring implant 100 being pushed downwards towards the distal end 112 of the bore (when the distal end 112 is supported in the bore). This novel configuration prevents the "piston effect" and therefore reduces the overall working distance of the bore or hole to allow deployment of the soft anchor 100 during surgery. As a result, the anchor assembly 100 can be more suitably used for surgeries involving small extremity bones.

It is also important to note that when tension is applied on the terminal ends 125A and 125B, each of the distal loops 122 also engages a thickness of a distal portion of the soft anchoring plant 100 which further assists with the axial shortening of the soft anchoring implant 100 when the terminal ends of the suture 120 are tensioned.

Figures 6A, 6B, 6C:
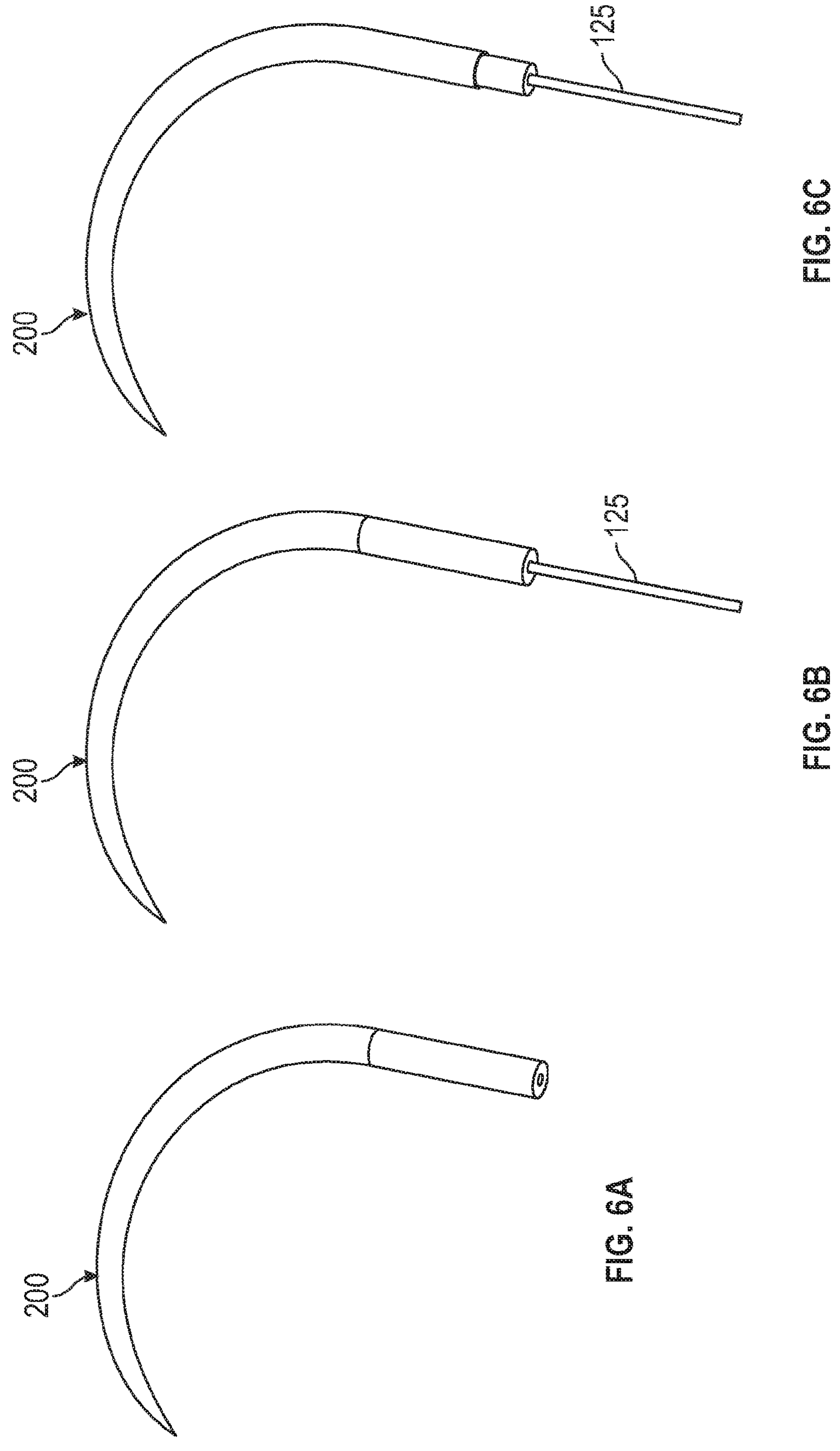
FIGS. 6A to 6C illustrate terminal ends 125 of the suture being attached to a surgical needle 200.

The terminal ends 125 of the suture 120 are attached to surgical needles 200 as shown in FIGS. 6A to 6C. The needles 200 comprises a piercing end and a suture receiving end which includes a hollow cavity that is suitably sized for receiving the terminal ends 125 of the suture 120. Upon insertion of the suture end 125 into the cavity, the walls of the cavity may be crimped for attachment of the suture ends 125A and 125B to corresponding needles 200.

In some embodiments, one of the terminal ends of the suture, namely the terminal end extending from the second suture segment may be turned and woven with a portion of the second segment into an internal portion of the implant. In such an embodiment, only one exiting terminal end may be used for fastening.

Figure 7:
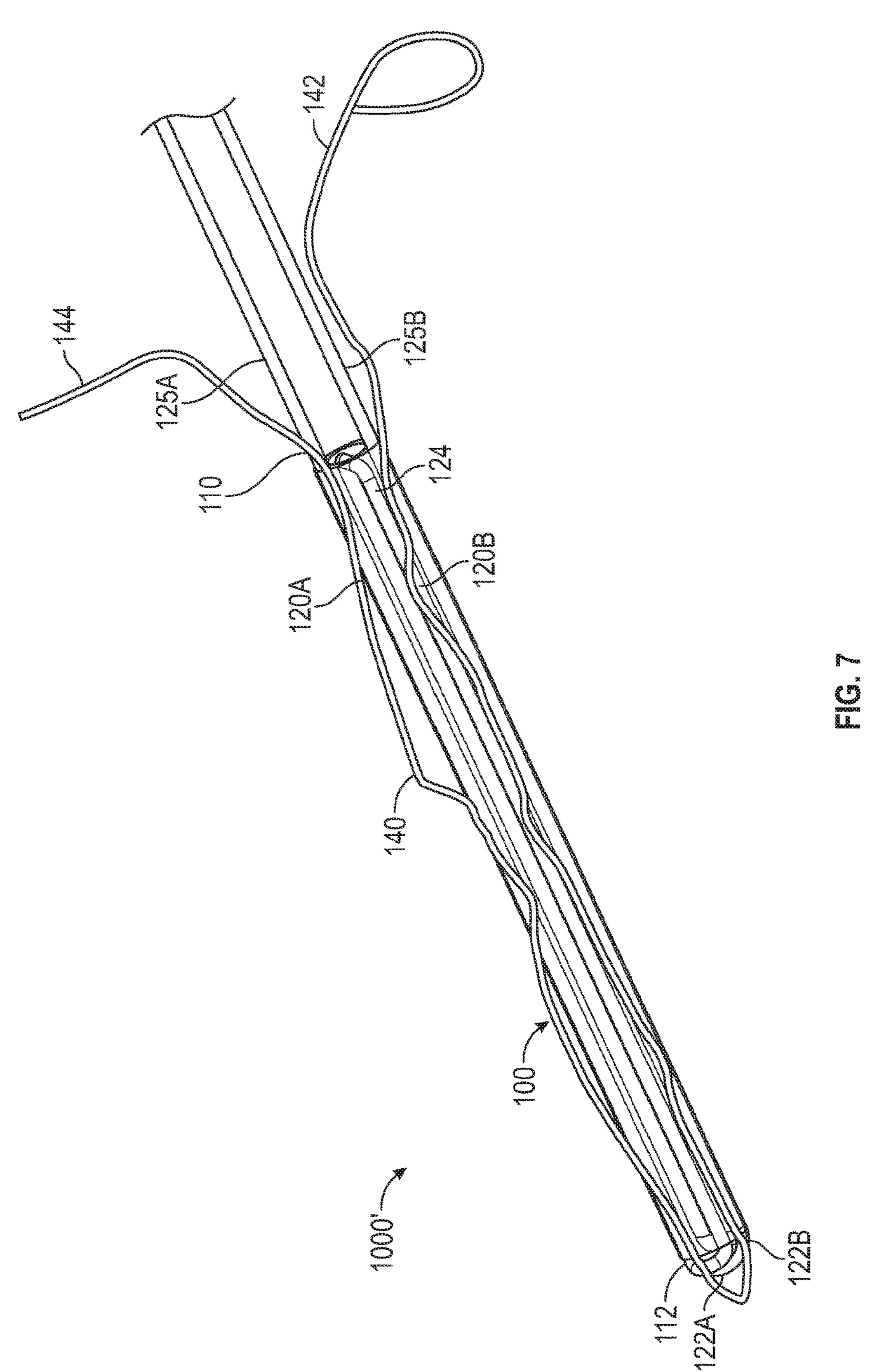
FIG. 7 is another embodiment of an anchor assembly 1000' in accordance with another embodiment.

Referring to FIG. 7, in another embodiment of the anchoring implant assembly 1000', an additional shuttle suture 140 that is separate from the primary suture 120 is provided. The shuttle suture 140 comprises one looped end 142 and one terminal end 144. During use, the shuttling suture 140 is useful to capture and carry one end of the primary fastening suture 120, through the looped end 142 back into the implant 100' by pulling the terminal end of the shuttle suture 140 thereby locking the primary suture (fastening suture) 120.

Figure 8:
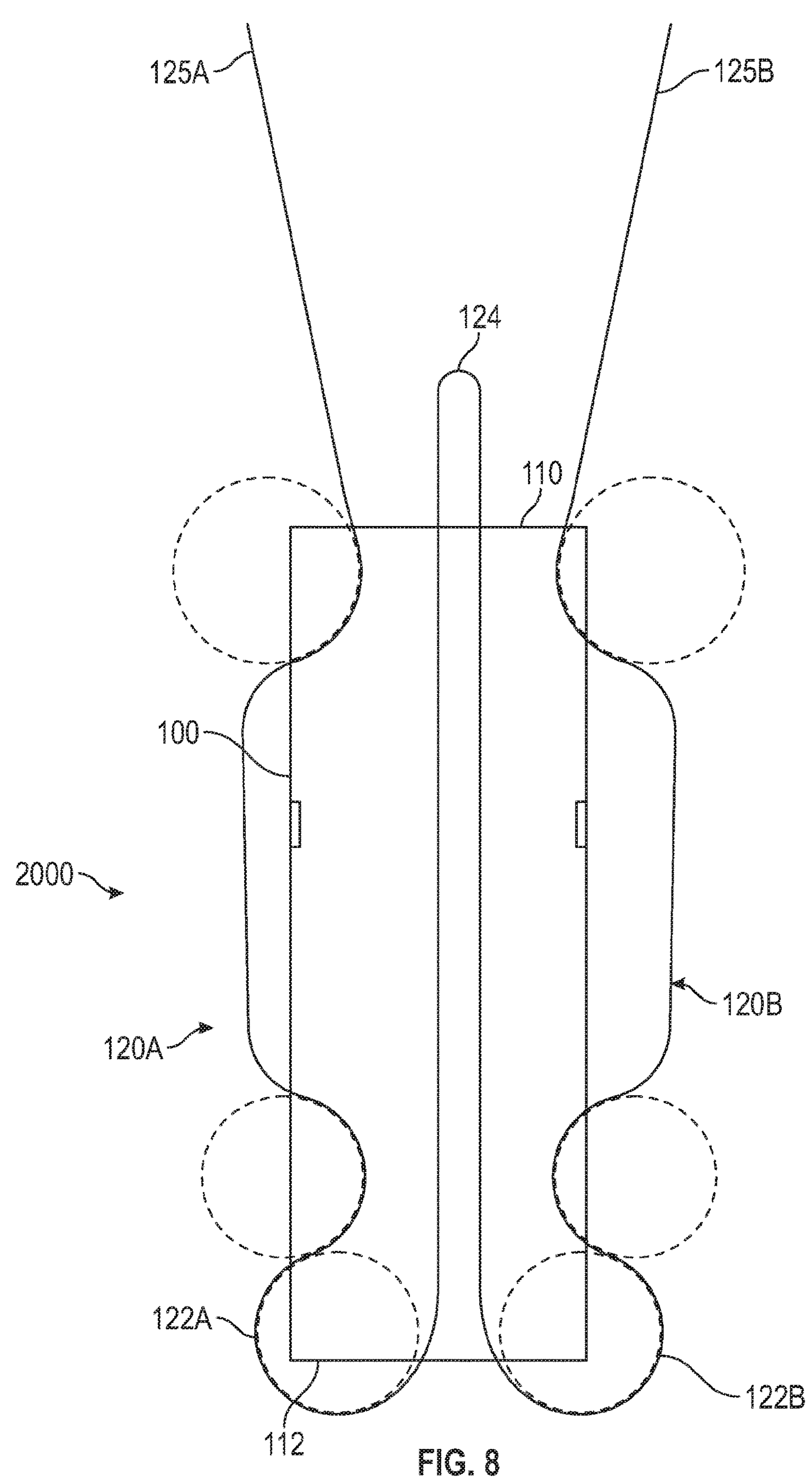
FIG. 8 is another embodiment of an anchor assembly 2000 in accordance with an embodiment.

Referring to FIG. 8, another embodiment of the anchoring implant assembly 3000 is illustrated. Like reference numerals denote like features that have been previously described. The flexible anchoring implant 100 shown in FIG. 9 also comprises a generally elongate configuration and extends between the proximal end 110 and the distal end 112. Suture 120 comprising continuous suture segments 120A and 120B that are passed through the walls of the flexible anchoring implant 100 in a novel manner. Specifically, a first segment 120A of the suture 120 is passed through an upper portion of the anchoring implant 100 in a general direction from the proximal end 110 towards the distal end 110 of the anchoring implant 100. The first suture segment 120A is inserted into and out of the proximal portion of the implant 100 to straddle an outer wall of the implant 100. The first suture segment is then inserted into and out of the distal portion of the implant 100.

The first segment is then looped around the distal end portion of the anchoring implant 100 by way of the distal loop 122A before returning the first segment 120A of the suture back towards the proximal end 110 of the anchoring implant 110. Unlike, the previously described embodiments, the suture segment 120A is not completely woven through the side wall of the anchoring implant 100. Instead, the first suture segment 120A is passed into and out of the upper portion of the anchoring implant 100 such that the suture 120 straddles the outer surface of the anchoring implant before being inserted into and out of a distal portion of the anchoring implant 100 that is adjacent the distal end of the anchoring implant 100. The first suture segment 120A then forms the first distal loop 122A to engage a thickness of the distal portion of the anchoring implant. The remaining part of the first suture segment is passed through an internal portion of the anchoring implant 100 and returned to the proximal end 110 of the anchoring implant 100 to form the bridging loop 124 before commending the second suture segment 120B. The second suture segment 120B extends from the bridging loop 124 towards the distal end 112 to form the second distal loop 122B that engages the thickness of the distal portion of the anchoring implant 100 before straddling the outer wall of the anchoring implant 100 to extend towards the proximal portion of the anchoring implant 100 where it forms a bridging loop 124 with the second suture segment 120B. The second suture segment extends from the proximal portion of the anchoring implant towards the distal portion of the anchoring implant 100 in a similar pattern as the first suture segment 120A to form the second distal loop 122B The second suture segment 122B follows a similar pattern as the first suture segment 122A and is inserted into and out of the distal portion of the anchoring implant 100 to straddle along the outer surface of the anchoring implant. The second suture segment is once again inserted into and out of the proximal portion of the anchoring implant 110 to allow the terminal end 125B to extend out of the proximal end 110 of the anchoring implant 100.

Once again, the novel configuration of the suture segments 120A and 120B being passed through the flexible anchoring implant 100 is such that applying tension to the terminal ends 125A and 125B of the suture 120, causes the flexible anchoring implant 100 to change shape from the elongate and radially narrow configuration into an axially shortened and radially extended configuration so as to deploy the anchoring implant 100 in the bore. Importantly, the provision of the bridging loop 124 at the proximal end 110 of the anchoring implant 100 in combination with the distal loops 124A and 124B results in the proximal end 110 of the soft anchoring implant 100 being pushed downwards towards the distal end 112 of the bore (when the distal end 112 is supported in the bore). This novel configuration prevents the "piston effect" and therefore reduces the overall working distance of the bore or hole to allow deployment of the soft anchor 100 during surgery. As a result, the anchor assembly 2000 can also be more suitably used for surgeries involving small extremity bones.

Figure 9:
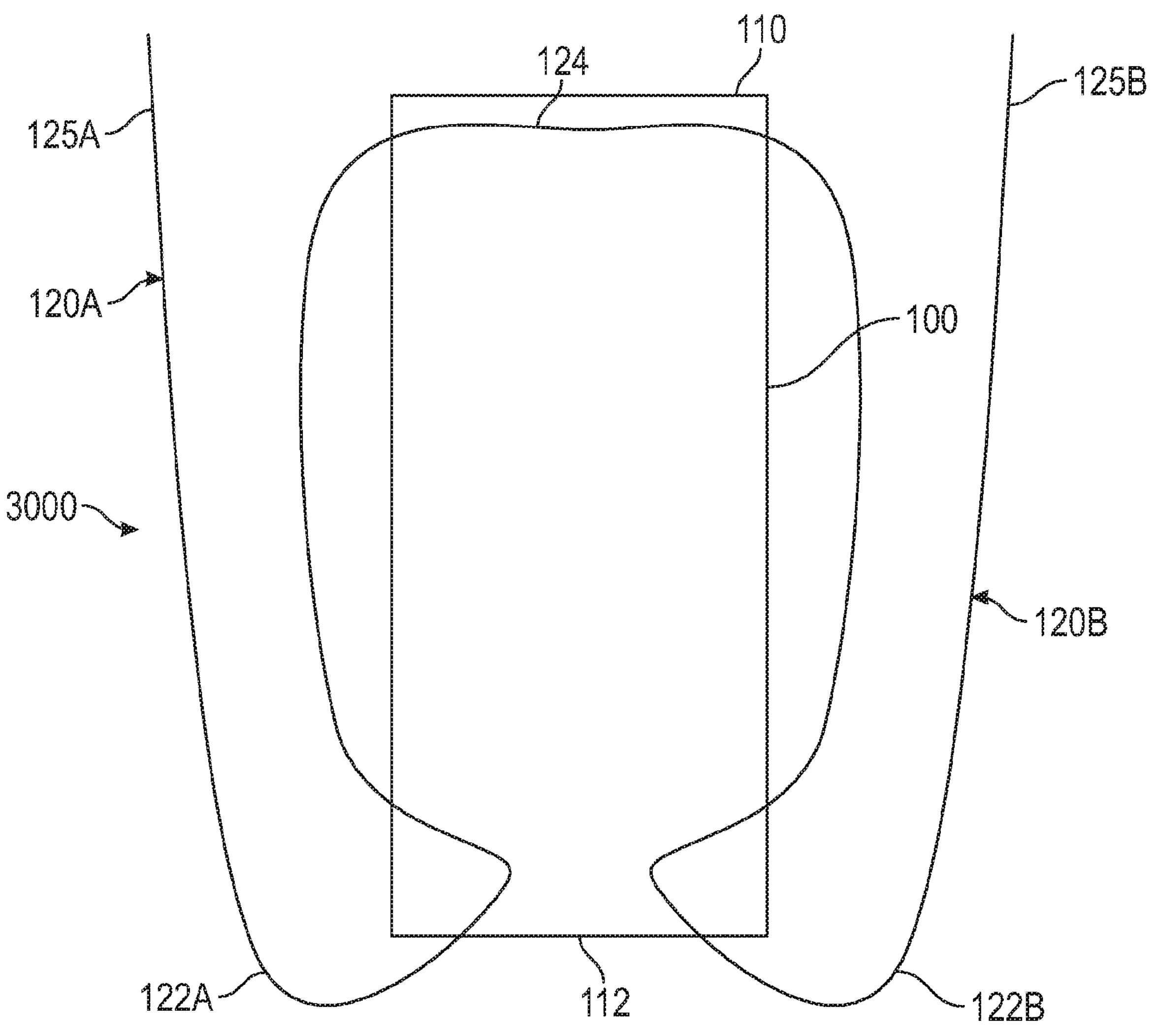
FIG. 9 is another embodiment of an anchor assembly 3000 in accordance with an embodiment.
Figure 10:
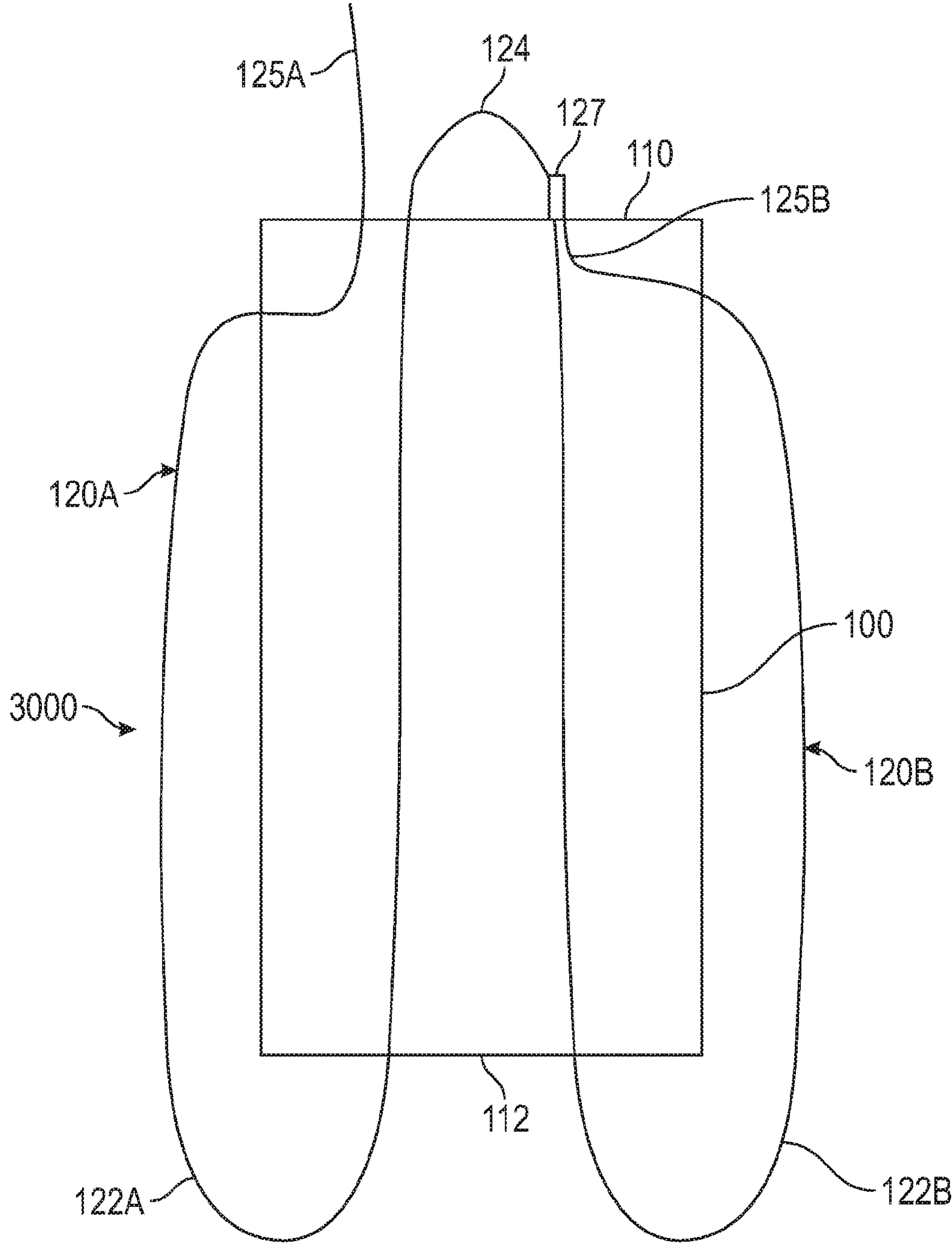
FIG. 10 is an alternative configuration of the anchor assembly 3000.

FIGS. 9 and 10 illustrate another possible embodiment of the anchoring implant assembly 3000. Like reference numerals denote like features that have been previously discussed in earlier sections.

The flexible anchoring implant 100 shown in FIG. 9 comprises a generally elongate configuration and extends between the proximal end 110 and the distal end 112. Suture 120 comprises continuous suture segments 120A and 120B that are passed through the walls of the flexible anchoring implant 100 in a novel manner. Specifically, a first segment 120A of the suture 120 is passed through the distal portion of the anchoring implant 100 in a general direction from the distal end 112 of the anchoring implant 100 towards the proximal end 110 of the implant 100. The first suture segment is passed into and out of the distal portion of the implant to form the first distal loop 122A which engages a thickness of the distal portion of the anchoring implant 100. The first suture segment 120A emerges out of the distal portion of the implant 100 to straddle an outer wall of the anchoring implant 100 before being passed into the proximal portion of the implant 100 to form the bridging loop 124 which is continuous with the second suture segment 120B.

The second suture segment 120B is follows a similar pattern as the first suture segment 120A and continues to extend from the proximal portion of the implant 100 towards the distal portion of the implant 100 by straddling the outer side wall of the anchoring implant 100 before being passed into and out of the distal portion of the implant 100 to form the second distal loop 122B which engages another thickness of the distal portion of the implant 100. The second terminal end 125B emerges out of the distal end portion of the implant 100.

The first segment is then looped around the distal end portion of the anchoring implant 100 by way of the distal loop 122A before returning the first segment 120A of the suture back towards the proximal end 110 of the anchoring implant 110. Unlike, the previously described embodiments, the suture segment 120A is not completely woven through the side wall of the anchoring implant 100. Instead, the first suture segment 120A is passed into and out of the upper portion of the anchoring implant 100 such that the suture 120 straddles the outer surface of the anchoring implant before being inserted into and out of a distal portion of the anchoring implant 100 that is adjacent the distal end of the anchoring implant 100. The first suture segment 120A then forms the first distal loop 122A to engage a thickness of the distal portion of the anchoring implant. The remaining part of the first suture segment is passed through an internal portion of the anchoring implant 100 and returned to the proximal end 110 of the anchoring implant 100 to form the bridging loop 124 before commending the second suture segment 122B. The second suture segment 122B extends from the bridging loop 124 towards the distal end 112 to form the second distal loop 122B that engages the thickness of the distal portion of the anchoring implant 100. The second suture segment 122B follows a similar pattern as the first suture segment 122A and is inserted into and out of the distal portion of the anchoring implant 100 to straddle along the outer surface of the anchoring implant. The second suture segment is once again inserted into and out of the proximal portion of the anchoring implant 110 to allow the terminal end 125B to extend out of the proximal end 110 of the anchoring implant 100.

Once again, the novel configuration of the suture segments 120A and 120B being passed through the flexible anchoring implant 100 is such that applying tension to the terminal ends 125A and 125B of the suture 120, causes the flexible anchoring implant 100 to change shape from the elongate and radially narrow configuration into an axially shortened and radially extended configuration so as to deploy the anchoring implant 100 in the bore. Importantly, the provision of the bridging loop 124 at the proximal end 110 of the anchoring implant 100 in combination with the distal loops 124A and 124B results in the proximal end 110 of the soft anchoring implant 100 being pushed downwards towards the distal end 112 of the bore (when the distal end 112 is supported in the bore) when the terminal ends 125A and 125B are pulled. This novel configuration prevents the "piston effect" and therefore reduces the overall working distance of the bore or hole to allow deployment of the soft anchor 100 during surgery. As a result, the anchor assembly 2000 can also be more suitably used for surgeries involving small extremity bones.

Turning to FIG. 10, in some embodiments the second terminal end 125B may be looped around itself using a loop 127 which allows the termina section comprising the terminal end 125B to be engaged and become fixed with the proximal portion of the anchoring implant 100 when the first terminal end 125A is pulled to transform the implant from its elongate axial configuration to the radially extended and axially shortened configuration.

Figure 11:
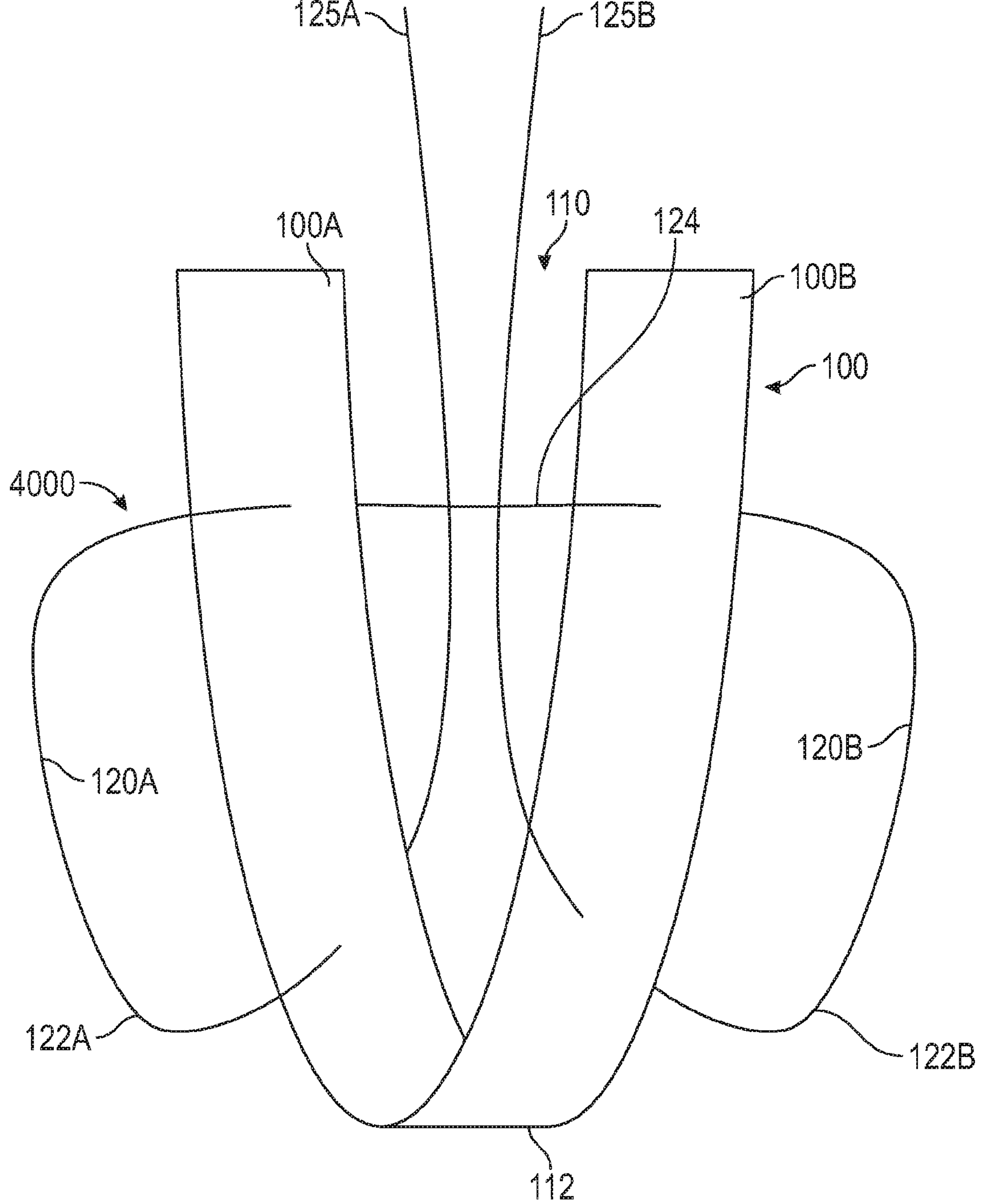
FIG. 11 is another embodiment of an anchor assembly 4000.

FIG. 11 illustrates yet another embodiment of the present disclosure in which like reference numerals denote like features that have been previously described. Unlike the previously described embodiments, the anchoring implant 100' comprises a flattened profile. In the preferred embodiment, the flat anchoring implant comprises a U-shaped configuration to extend between proximal end 110 and distal end 112. The first suture segment 120A comprises continuous suture segments 120A and 120B that are passed through the walls of the flexible anchoring implant 100 in a novel manner. Specifically, a first segment 120A of the suture 120 is passed through the distal portion of the anchoring implant 100 in a general direction from the distal end 112 of the anchoring implant 100 towards the proximal end 110 of the implant 100. The first suture segment 120A is passed into and out of the distal portion of the implant to form the first distal loop 122A which engages a thickness of the distal portion of the anchoring implant 100'. The first suture segment 120A emerges out of the distal portion of the implant 100' to straddle an outer wall of the anchoring implant 100 before being passed into the proximal portion of the implant 100' to form the bridging loop 124 which is continuous with the second suture segment 120B.

The second suture segment 120B follows a similar pattern as the first suture segment 120A and continues to extend from the proximal portion of the implant 100' towards the distal portion of the implant 100' by straddling the outer side wall of the anchoring implant 100' before being passed into and out of the distal portion of the implant 100' to form the second distal loop 122B which engages another thickness of the distal portion of the implant 100'. The second terminal end 125B emerges out of the distal end portion of the implant 100'.

The first segment is then looped around the distal end portion of the anchoring implant 100' by way of the distal loop 122A before returning the first segment 120A of the suture back towards the proximal end 110 of the anchoring implant 110. The suture segment 120A is not completely woven through the side wall of the anchoring implant 100. Instead, the first suture segment 120A is passed into and out of the upper portion of the flat anchoring implant 100' such that the suture 120 straddles the outer surface of the first limb 100A of the anchoring implant 100' before being inserted into and out of a distal portion of the anchoring implant 100 that is adjacent the distal end of the anchoring implant 100. The first suture segment 120A then forms the first distal loop 122A to engage a thickness of the distal portion in a first limb (100A) of the anchoring implant. The remaining part of the first suture segment 120A is passed between the two limbs defining the U-shaped construct of the anchoring implant 100' and returned to the proximal end 110 of the anchoring implant 100 to form the bridging loop 124 before commencing the second suture segment 122B. The second suture segment 122B extends from the bridging loop 124 towards the distal end 112 to form the second distal loop 122B that engages the thickness of the distal portion of the second limb (100B) of the anchoring implant 100. The second suture segment 122B follows a similar pattern as the first suture segment 122A and is inserted into and out of the distal portion of the second limb 100B of the anchoring implant 100 to straddle along the outer surface of the second limb 100B anchoring implant. The second suture segment 120B is once again inserted into and out of the proximal portion of the anchoring implant 110 to allow the terminal end 125B to extend out of the proximal end 110 of the anchoring implant 100.

As with the previously described embodiments, the implant assembly 4000 also provides the novel configuration of the suture segments 120A and 120B being passed through the flat flexible anchoring implant 100 (with the two limbs 100A and 100B) is such that applying tension to the terminal ends 125A and 125B of the suture 120, causes the flexible anchoring implant 100 to change shape from the elongate and radially narrow configuration into an axially shortened and radially extended configuration so as to deploy the anchoring implant 100 in the bore. Provision of the bridging loop 124 at the proximal end 110 of the anchoring implant 100 in combination with the distal loops 124A and 124B results in the proximal end 110 of the soft anchoring implant 100 being pushed downwards towards the distal end 112 of the bore (when the distal end 112 is supported in the bore) when the terminal ends 125A and 125B are pulled. This novel configuration prevents the "piston effect" and therefore reduces the overall working distance of the bore or hole to allow deployment of the soft anchor 100 during surgery.

In compliance with the statute, the disclosure has been described in language more or less specific to structural or methodical features. The term "comprises" and its variations, such as "comprising" and "comprised of" is used throughout in an inclusive sense and not to the exclusion of any additional features.

It is to be understood that the disclosure is not limited to specific features shown or described since the means herein described comprises preferred forms of putting the disclosure into effect.

The disclosure is, therefore, claimed in any of its forms or modifications within the proper scope of the appended claims appropriately interpreted by those skilled in the art.

The invention claimed is:

1. An anchor assembly for securing a tissue to a bone or tissue, the anchor comprising:

an elongate and flexible anchoring implant for inserting into a bore of the bone or the tissue, the anchoring implant comprising a proximal end and a distal end with sidewalls extending therebetween, a suture comprising: a first suture segment extending between the proximal and distal ends of the implant, the first suture segment being passed through a first side wall portion of the implant; a second suture segment extending between the proximal and distal ends of the implant, the second suture segment being passed through a second side wall portion of the implant; a bridging loop extending between the first suture segment and the second suture segment, the bridging loop being located at or adjacent an in-use upper portion of the anchoring implant that includes the proximal end of the anchoring implant; and wherein each of the first and second suture segments comprises respective terminal ends of the suture that extend from the anchor implant;

wherein applying tension to one or both of the terminal ends of the suture, when the anchoring implant is located in the bone or the tissue, causes the proximal end of the flexible anchoring implant to be drawn towards the distal end of the anchoring implant to effect change of shape of the implant from an elongate and radially narrow configuration into an axially shortened and radially extended configuration so as to deploy the anchoring implant in the bore, and wherein each of the first and second suture segments comprises a respective distal loop to engage a thickness of an in-use lower portion of the anchoring implant when the terminal ends of the suture are tensioned.

2. An anchor assembly in accordance with claim 1, wherein the respective terminal ends of the suture extend from or adjacent the proximal end of the anchor implant.

3. An anchor assembly in accordance with claim 2, wherein the respective distal loops engage a thickness of the distal end portion of the anchoring implant when the terminal ends of the suture are tensioned.

4. An anchor assembly in accordance with claim 2, wherein each of the first and second suture segments comprises:

a first weave extending axially along the walls of the anchoring implant in a direction from the proximal end of the anchoring implant towards the distal end of the anchoring implant;

a second weave extending axially along the walls of anchoring implant in a direction from the distal end of the anchoring implant towards the proximal end of the anchoring implant; and wherein the first and second weave for each suture segment are separated by the respective distal loop of the suture segment.

5. An anchor assembly in accordance with claim 4, wherein the first and second weave for each suture segment are spaced apart from each other.

6. An anchor assembly in accordance with claim 4, wherein the first and second weave for the first suture segment are spaced apart from the first and second weave for the second suture segment.

7. An anchor assembly in accordance with claim 1, wherein upon tensioning the terminal ends of the suture, the bridging loop engages a thickness of the upper portion of the anchoring implant.

8. An anchor assembly in accordance with claim 7 wherein upon tensioning the terminal ends of the suture, the bridging loop engages a circumferential edge of the proximal end portion of the anchoring implant.

9. An anchor assembly in accordance with claim 1, wherein the first and second suture segments are continuous with each other.

10. An anchor assembly in accordance with claim 1, wherein the distal end of the anchor implant is closed.

11. An anchor assembly in accordance with claim 1, wherein the terminal ends of the suture are attached to a respective surgical needle.

12. An anchor assembly in accordance with claim 1, wherein the anchoring implant comprises a braided structure.

13. An anchor assembly in accordance with claim 1, wherein the anchoring implant comprises a cylindrical structure in the elongate and radially narrow configuration.

14. An anchor assembly in accordance with claim 1, wherein the anchoring implant comprises a hollow tubular structure in the elongate and radially narrow configuration.

15. An anchor assembly in accordance with claim 1, wherein the suture comprises biodegradable materials.

16. An anchor assembly in accordance with claim 1, wherein in the terminal end of the second suture segment is turned and woven with a portion of the second segment into an internal portion of the implant.

* * * * *